(12) United States Patent
Dingli et al.

(10) Patent No.: US 11,357,745 B2
(45) Date of Patent: Jun. 14, 2022

(54) METHODS AND MATERIALS FOR TREATING CYTOKINE RELEASE SYNDROME

(71) Applicant: Mayo Foundation for Medical Education and Research, Rochester, MN (US)

(72) Inventors: David Dingli, Rochester, MN (US); Ameet K. Mishra, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 244 days.

(21) Appl. No.: 16/548,215

(22) Filed: Aug. 22, 2019

(65) Prior Publication Data
US 2020/0069615 A1  Mar. 5, 2020

Related U.S. Application Data

(60) Provisional application No. 62/724,930, filed on Aug. 30, 2018.

(51) Int. Cl.
*A61K 31/155* (2006.01)
*A61P 35/00* (2006.01)
*A61K 39/395* (2006.01)

(52) U.S. Cl.
CPC ........ *A61K 31/155* (2013.01); *A61K 39/3955* (2013.01); *A61P 35/00* (2018.01)

(58) Field of Classification Search
CPC ... A61K 31/155; A61K 39/3955; A61P 35/00; C07K 16/2866
See application file for complete search history.

(56) References Cited

PUBLICATIONS

Afzal, et al Journal for Immunotherapy of Cancer 6, Article No. 64 (2018) (Year: 2018).*
Ceschi, et al Front. Pharmacol., May 4, 2020 (Year: 2020).*
Mishra, et al Blood Cancer Journal Article:3 Issue: 1 vol. 11 (2021) (Year: 2021).*
Aydemir, et al, Clin Cancer Res. Mar. 1, 2015; 21(5): 1161-1171 (Year: 2015).*
NCI: CAR T Cells: Expanding into Multiple Myeloma Jun. 12, 2017 (Year: 2017).*
Shimbakuro-Vornhagen, et al J Immunother Cancer Jun. 15, 2018;6(1):56 (Year: 2018).*
Rawstron, et al. Blood, Dec. 1, 2000 vol. 96, No. 12 (Year: 2000).*
Afzal, et al., Journal for ImmunoTherapy of Cancer (2018) 6:64 (Year: 2018).*
Mu et al., OncoTargets and Therapy 2018:11 1767-1776 (Year: 2018).*
Rotz, et al., Pediatr. Blood Cancer 2017 vol. 64 (Year: 2017).*
Hirsch, et al., 2013 PNAS vol. 110 No. 3 972-977 (Year: 2013).*
Yan, et al., Molecular Medicine 2018 24:20 (Year: 2018).*
Aharaz et al., "Risk of lactic acidosis in type 2 diabetes patients using metformin: A case control study," PLoS One., 13(5):e0196122, 2018.
Andrzejewski et al., "Metformin directly acts on mitochondria to alter cellular bioenergetics," Cancer Metab., 2(1):12, Dec. 2014.
Aruna et al., "Metformin therapy in women with polycystic ovary syndrome," Int. J. Gynaecol. Obstet., 87(3):237-41, Dec. 2004.
Ben et al., "Metformin, independent of AMPK, induces mTOR inhibition and cell-cycle arrest through REDD1," Cancer Res., 71(13):4366-72, Jul. 2011.
Bergsagel and Chesi, "Molecular classification and risk stratification of myeloma," Hematol Oncol., 31(Suppl 1):38-41, Jun. 2013.
Bost et al., "Metformin and cancer therapy," Curr. Opin. Oncol., 24(1):103-8, Jan. 2012.
Boursi et al., "Impact of metformin on the progression of MGUS to multiple myeloma," Leuk. Lymphoma., 58(5):1265-7, May 2017.
Chang et al., "Association between metformin use and progression of monoclonal gammopathy of undetermined significance to multiple myeloma in US veterans with diabetes mellitus: a population-based retrospective cohort study," Lancet Haematol., 2(1):e30-6, Jan. 2015.
Choi and Park, "Metabolic roles of AMPK and metformin in cancer cells," Mol. Cells, 36(4):279-87, Oct. 2013.
Davila et al., "Efficacy and toxicity management of 19-28z CAR T cell therapy in B cell acute lymphoblastic leukemia," Sci. Transl. Med., 6(224):224ra25, Feb. 2014.
Dispenzieri et al., "The clinical spectrum of Castleman's disease," Am. J. Hematol., 87(11):997-1002, Nov. 2012.
French et al., "Analysis of IL-6-mediated growth control of myeloma cells using a gp130 chimeric receptor approach," Leukemia, 16(6):1189-96, Jun. 2002.
French et al., "Dissection of the signalling requirements of interleukin-6-stimulated myeloma cell growth," Acta. Oncol., 39(7):777-81, Jan. 2000.
Frey and Porter, "Cytokine Release Syndrome With Novel Therapeutics for Acute Lymphoblastic Leukemia," Hematology Am. Soc. Hematol. Educ. Program, 2016(1):567-572, Dec. 2016.
Giavridis et al., "CAR T cell-induced cytokine release syndrome is mediated by macrophages and abated by IL-1 blockade," Nat. Med., 24(6):731-8, Jun. 2018.
Horiuchi et al., "Metformin Directly Binds the Alarmin HMGB1 and Inhibits Its Proinflammatory Activity," J. Biol. Chem., 292(20):8436-46, May 2017.
Jelinek, "Mechanisms of myeloma cell growth control," Hematol. Oncol. Clin. North Am., 13(6):1145-57, Dec. 1999.
Jordan et al., "Interleukin-6, A Cytokine Critical to Mediation of Inflammation, Autoimmunity and Allograft Rejection: Therapeutic Implications of IL-6 Receptor Blockade," Transplantation, 101(1):32-44, Jan. 2017.
Mihara et al., "IL-6/IL-6 receptor system and its role in physiological and pathological conditions," Clin. Sci., 122(4):143-59, Feb. 2012.

(Continued)

*Primary Examiner* — Julie Wu
*Assistant Examiner* — John L Van Druff
(74) *Attorney, Agent, or Firm* — Fish & Richardson P.C.

(57) ABSTRACT

This document relates to methods and materials involved in treating a mammal having, or at risk of developing, cytokine release syndrome (CRS). For example, a mammal having, or at risk of developing, CRS can be treated by administering one or more biguanides (e.g., metformin) to the mammal.

11 Claims, 8 Drawing Sheets

(56) References Cited

PUBLICATIONS

Munshi et al., "Consensus recommendations for risk stratification in multiple myeloma: report of the International Myeloma Workshop Consensus Panel 2," Blood, 117(18):4696-700, 2011.

Norelli et al., "Monocyte-derived IL-1 and IL-6 are differentially required for cytokine-release syndrome and neurotoxicity due to CAR T cells," Nat. Med., 24(6):739-48, Jun. 2018.

Park et al., "Long-term follow-up of CD19 CAR therapy in acute lymphoblastic leukemia," N. Engl. J. Med., 378(5):449-59, Feb. 2018.

Porter et al., "Grading of Cytokine Release Syndrome Associated With the CAR T Cell Therapy Tisagenlecleucel," J. Hematol. Oncol., 11(1):35, Mar. 2018.

Saengboonmee et al., "Metformin exerts antiproliferative and antimetastatic effects against cholangiocarcinoma cells by targeting STAT3 and NF-κB," Anticancer Res., 37(1):115-23, Jan. 2017.

Shimabukuro-Vornhagen et al., "Cytokine Release Syndrome," J. Immunother. Cancer, 6(1):56, Jun. 2015.

de Souza Teixeira et al., "Short-term treatment with metformin reduces hepatic lipid accumulation but induces liver inflammation in obese mice," Inflammopharmacology, Feb. 2018, 26(4):1103-1115.

Wang et al., "Effects of metformin treatment on serum levels of C-reactive protein and interleukin-6 in women with polycystic ovary syndrome: a meta-analysis," Medicine, Sep. 2017, 96(39):e8183, 12 pages.

Wang et al., "Metformin does not reduce inflammation in diabetics with abdominal aortic aneurysm or at high risk of abdominal aortic aneurysm formation," Vascular, Jun. 2018, 26(6):608-614.

\* cited by examiner

METHODS AND MATERIALS FOR TREATING CYTOKINE RELEASE SYNDROME

CROSS-REFERENCE TO RELATED APPLICATIONS

This application claims the benefit of U.S. Provisional Application Ser. No. 62/724,930, filed Aug. 30, 2018. The disclosure of the prior application is considered part of (and is incorporated by reference in) the disclosure of this application.

BACKGROUND

1. Technical Field

This document relates to methods and materials involved in treating a mammal having, or at risk of developing, cytokine release syndrome (CRS). For example, a mammal having, or at risk of developing, CRS can be treated by administering one or more biguanides (e.g., metformin) to the mammal.

2. Background Information

CRS is a potentially life-threatening condition characterized by high fever and hypotension that may progress to multi-organ failure including distributive shock due to systemic capillary leak, renal failure and respiratory failure that may lead to death (Porter et al., *J Hematol Oncol.* 2018; 11(1):35). CRS is a potential complication of chimeric antigen receptor T cell (CAR-T) therapy as well as the use of bispecific T-cell engagers (BiTE) such as blinatumumab (e.g., BLINCYTO®) (Shimabukuro-Vornhagen et al., *J Immunother Cancer.* 2018; 6(1):56; and Horiuchi et al., *J Biol Chem.* 2017; 292(20):8436-46). Perhaps 20% or more of patients with hematologic malignancies treated with CAR-T cells end up in the intensive care unit for CRS (Park et al., *N Engl J Med.* 2018; 378(5):449-59).

SUMMARY

This document provides methods and materials for treating a mammal having, or at risk of developing, CRS. For example, a mammal having, or at risk of developing, CRS can be treated by administering one or more biguanides (e.g., metformin) to the mammal. As demonstrated herein, IL-6 receptor alpha (IL-6Rα; also known as CD126) expression on the surface of a cancer cell can indicate that the cancer cell is likely to respond to metformin. Also as demonstrated herein, metformin (a biguanide antihyperglycemic agent) can down-regulate IL-6R expression on the surface of cells, and can prevent C-reactive protein (CRP) release from the liver in response to IL-6 stimulation of hepatocytes.

Patients are only treated for CRS once they meet certain criteria (e.g., a certain severity of the CRS). In addition, patients having an infection and CRS are typically excluded from CRS treatment since these patients are typically neutropenic and present with high fever. Having the ability to treat and/or prevent CRS as described herein provides an opportunity to administer immunotherapies (e.g., cancer immunotherapies such as BiTE technology and CAR-T cell therapy) with a reduced risk of developing CRS.

In general, one aspect of this document features methods for treating a mammal having CRS. The methods can include, or consist essentially of, administering to a mammal in need thereof (e.g., a mammal having CRS) a composition including a biguanide, where the severity of the CRS is reduced within the mammal. The mammal can be a human. The biguanide can be metformin. The CRS can be associated with an immunotherapy. The immunotherapy can include CAR-T cell therapy. The immunotherapy can include BiTE therapy. The BiTE therapy can include administering blinatumumab to the mammal.

In another aspect, this document features a method for treating a mammal at risk of developing CRS, where the mammal is scheduled to undergo immunotherapy. The methods can include, or consist essentially of, administering to a mammal in need thereof (e.g., a mammal at risk of developing CRS) a composition comprising a biguanide. The mammal can be a human. The biguanide can be metformin. The CRS can be associated with an immunotherapy. The immunotherapy can include CAR-T cell therapy. The immunotherapy can include BiTE therapy. The BiTE therapy can include administering blinatumumab to the mammal. The composition including the biguanide can be administered to the mammal prior to the immunotherapy. The composition including the biguanide can be administered to the mammal concurrent with the immunotherapy. In some cases, the mammal does not develop said CRS following the administering step.

In another aspect, this document features a method for treating a mammal having cancer, where the cancer includes cancer cells having IL-6R polypeptides on the surface of the cancer cells. The methods can include, or consist essentially of, administering to a mammal in need thereof (e.g., a mammal having cancer), a composition including a biguanide. The mammal can be a human. The IL-6R polypeptides can be IL-6Rα polypeptides. The cancer can be a blood cancer. The blood cancer can be a multiple myeloma. The method also can include administering an agent used to reduce levels of IL-6R polypeptides to the mammal. The agent can be an anti-IL-6R antibody. The anti-IL-6R antibody can be tocilizumab. The mammal can be identified as having cancer cells having IL-6R polypeptides on the surface of the cancer cells. The method can include identifying the mammal as having cancer cells having IL-6R polypeptides on the surface of the cancer cells.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 4A-4D show that metformin induced apoptosis and inhibition of cell cycle progression in myeloma cells independent of their underlying genetic abnormalities. (A) HMCLs were stained with IL-6Rα-PE and IL-6 signal transducer (IL-6ST)-APC antibodies and median fluorescence intensity was determined for expression of cell surface markers using flow cytometry. Data is presented as heat map intensity corresponding to the level of expression. (B) HMCLs were treated with different doses of metformin for 72 hours and relative proliferation compared to vehicle control was calculated using MTT assay. Data is presented as $IC_{50}$ for different cell lines and $IC_{50}$ was calculated using Compusyn software (n=6). (C) & (D) HMCLs MM1S, RPMI, and U266 were treated with vehicle control (DMSO) or metformin 10 mM for 72 hours. (C) For apoptosis assay, cells were suspended in Annexin V buffer and stained with Annexin V for 30 minutes. Propidium iodide was added 10 minutes prior to data acquisition by flow cytometry. (D) For cell cycle assay, BrdU was added and incubated for 4 hours. Cells were fixed, permeabilized and stained with Anti-BrdU antibody for 30 minutes. 7AAD was added 10 minutes to samples before data acquisition by flow cytometry. The data were acquired on BD Fortessa and analyzed with flowjo V10.

FIGS. 5A-5F show that IL-6Rα expression on the myeloma cell surface predicted for response to metformin therapy and can serve as a biomarker for therapeutic response. Ten different HMCLs were treated with metformin (0, 1 mM, 5 mM, 10 mM, 20 mM, 40 mM, and 80 mM) for 72 hours. The total numbers of live cells (metabolically active) were estimated using MTT assay. Relative proliferation was calculated by normalizing absorbance value with that obtained for vehicle control. $IC_{50}$ was calculated using Compusyn software. Basal cell surface expression of IL-6Rα and IL-6ST was determined using flow cytometry. (A) Median fluorescence intensity (MFI) for IL-6Rα was plotted against metformin $IC_{50}$ for different HMCLs (n=6 for $IC_{50}$ and n=3 for MFI) and the correlation determined (significant, negative correlation, p=0.0045). (B) MFI for IL-6ST was plotted against metformin $IC_{50}$ for different HMCLs (n=6 for IC50 and n=3 for MFI) and correlation determined (not significant, p=0.7009). (C) IL-6Rα was knocked-down (KD) using two different ShRNA against IL-6Rα. Decreased expression for IL-6Rα was confirmed with flow cytometry. (D) JJN3 IL-6Rα over-expressing cells were created using IL-6R cDNA expressing vector. Increased expression of IL-6Rα was confirmed by flow cytometry. (E) The sensitivity to metformin ($IC_{50}$) was calculated using the MTT assay for cells transduced with the shRNA scrambled control or IL-6Rα KDs (n=6). Knockdown of IL-6Rα reduced the sensitivity (increased the $IC_{50}$) of RPMI cells to metformin compared to baseline. (F) Metformin $IC_{50}$ was calculated using MTT assay for JJN3 control and IL-6Rα over-expresser (n=6). Overexpression of IL-6Rα increased the sensitivity (decreased the $IC_{50}$) of the JJN3 cells to metformin.

DETAILED DESCRIPTION

This document provides methods and materials for treating a mammal having, or at risk of developing, CRS. For example, one or more biguanides (e.g., metformin) can be administered to a mammal having CRS to treat the mammal.

In some cases, one or more biguanides (e.g., metformin) can be administered to a mammal at risk of developing CRS to treat the mammal.

Any appropriate mammal having, or at risk of developing, CRS can be treated as described herein. Examples of mammals having, or at risk of developing, CRS that can be treated as described herein (e.g., by administering one or more biguanides such as metformin to the mammal) include, without limitation, humans, non-human primates (e.g., monkeys), dogs, cats, horses, cows, pigs, sheep, mice, and rats. For example, a human having, or at risk of developing, CRS can be treated by administering metformin to that human.

When treating a mammal (e.g., a human) having, or at risk of developing, CRS as described herein (e.g., by administering one or more biguanides such as metformin to the mammal), the CRS can be any type of CRS. In cases where a mammal has CRS, the CRS can be any severity of CRS (e.g., Grade 1, Grade 2, Grade 3, Grade 4, or Grade 5). In some cases, a CRS can be associated with administration of (e.g., can be a complication of) an immunotherapy. Immunotherapy can be a cancer immunotherapy. Examples of immunotherapies include, without limitation, adoptive T cell therapies (e.g., CAR-T cell therapies such as tisagenlecleucel and axicabtagene ciloleucel), antibody therapies (e.g., BiTE therapies such as blinatumumab and solitomab), and immune effector cell therapies. In some cases, CRS can be associated with an autoimmune disease and/or a complication of an autoimmune disease (e.g., an arthritis such as rheumatoid arthritis and giant cell arteritis, and macrophage activation syndrome). In some cases, CRS can be associated with transplant rejection (e.g., organ rejection, allograft rejection (e.g., allograft rejection after an allogeneic transplant such as a haploidentical transplant), host-versus-graft disease, and graft-versus-host disease (GVHD)). In some cases, CRS can be associated with an infection (e.g., bacterial infections such as gram-positive bacterial infections and gram-negative bacterial infections, viral infections, protozoan infections, and infections from higher organism such as helminthes).

In cases where a CRS is associated with an immunotherapy, and the immunotherapy is a cancer immunotherapy, the cancer can be any type of cancer. In some cases, a cancer can include one or more solid tumors. In some cases, a cancer can be a blood cancer. Examples of cancers that can be treated by a cancer immunotherapy include, without limitation, multiple myeloma (e.g., smoldering multiple myeloma), acute lymphoblastic leukemias (ALLs), chronic lymphocytic leukemias (CLLs), Hodgkin's lymphomas, non-Hodgkin's lymphomas, Waldenstrom's macroglobulinemia, hairy cell leukemia, and primary amyloidosis (AL, AH, or AHL).

In cases where a CRS is associated with an immunotherapy, the immunotherapy can target any appropriate antigen. Examples of antigens that can be targeted by an immunotherapy include, without limitation, CD19, CD20, CD47, epithelial cell adhesion molecule (EpCAM), B cell maturation antigen (BCMA), CD38, CD30, and epidermal growth factor receptor (EGFR).

In some cases, methods described herein can include identifying a mammal (e.g., a human) as having CRS. Any appropriate method can be used to identify a mammal having CRS. For example, detection of elevated levels of biomarkers (e.g., cytokines such as IL-6, IFNγ, TNF-α, KC, MIP-2, and/or MIP-1β; ferritin; C-reactive protein; and fibrinogen) can be used to identify a mammal having CRS. Any appropriate method can be used to detect elevated levels of biomarkers. Examples of methods that can be used to detect elevated levels of biomarkers include, without limitation, western blotting techniques, enzyme-linked immunosorbent assay (ELISA), real-time polymerase chain reaction (PCR), flow cytometry, mass spectrometry, and a Luminex assay.

In some cases, methods described herein can include identifying a mammal (e.g., a human) as being at risk of developing CRS. For example, a mammal undergoing, or scheduled to undergo, immunotherapy can be at risk of developing CRS. For example, a mammal undergoing, or scheduled to undergo, a transplant can be at risk of developing CRS. For example, a mammal having high levels of proteins that are released by the liver (e.g., proteins that are released by the liver in response to elevated levels of circulating IL-6 levels such as CRP and ferritin) can be at risk of developing CRS.

Once identified as having, or as being at risk for developing, CRS, a mammal (e.g., a human) can be administered, or instructed to self-administer, one or more biguanides. For example, one or more biguanides can be administered to a mammal in need thereof. A biguanide can be any appropriate biguanide. In some cases, a biguanide can be an antihyperglycemic biguanide. In some cases, a biguanide can be an inhibitor of 5' adenosine monophosphate activated protein kinase (AMPK) polypeptide expression. In some cases, a biguanide can be an inhibitor of AMPK polypeptide activity. Examples of biguanides that can be used as described herein (e.g., to treat a mammal having, or at risk of developing, CRS) include, without limitation, metformin, phenformin, buformin, and derivatives thereof. For example, a mammal having, or at risk for developing, CRS can be administered or can self-administer metformin.

When treating a mammal having, or at risk of developing, CRS, one or more biguanides (e.g., metformin) can be administered to the mammal at any appropriate time. For example, when a mammal at risk of developing CRS is undergoing, or scheduled to undergo, immunotherapy, one or more biguanides can be administered before, during (e.g., concurrent with), and/or after the immunotherapy. For example, when a mammal at risk of developing CRS is undergoing, or scheduled to undergo, a transplant, one or more biguanides can be administered before, during (e.g., concurrent with), and/or after the immunotherapy.

In some cases, treating a mammal having, or at risk for developing, CRS as described herein (e.g., by administering one or more biguanides such as metformin to the mammal) can be effective to reduce the severity of the CRS and/or to reduce or eliminate one or more symptoms of the CRS. In some cases, the severity of CRS can be determined by the grade (e.g., Grade 1, Grade 2, Grade 3, Grade 4, and Grade 5) of the CRS. In some cases, the severity of CRS can be as described elsewhere (see, e.g., Porter et al, 2018, *J Hematol Oncol.* 11:35). Examples of symptoms of CRS include, without limitation, fever, fatigue, loss of appetite, muscle and joint pain, nausea, vomiting, diarrhea, rashes, fast breathing, rapid heartbeat, low blood pressure, seizures, headache, confusion, delirium, hallucinations, tremor, loss of coordination, low blood oxygen, widened pulse pressure, altered cardiac output (e.g., increased cardiac output in early CRS and decreased cardiac output in late CRS), high blood nitrogen levels, elevated levels of D-dimer polypeptides, elevated levels of transaminases, factor I deficiency, excessive bleeding, elevated levels of bilirubin, elevated levels of CRP, elevated levels of ferritin, elevated levels of IL-6, and elevated levels of fibrinogen. In some cases, a symptom of CRS can be as described elsewhere (see, e.g., Frey et al., 2016, *Hematology Am Soc Hematol Educ Program.* 2016: 567-572).

In some cases, when treating a mammal having, or at risk for developing, CRS associated with a cancer immunotherapy as described herein (e.g., by administering one or more biguanides such as metformin to the mammal), the treatment can reduce one or more symptoms of the cancer in the mammal. For example, the treatment can reduce the number of cancer cells within a mammal. For example, the treatment can reduce the size (e.g., volume) of one or more tumors within a mammal.

In some cases, when treating a mammal having, or at risk of developing CRS, as described herein (e.g., by administering one or more biguanides such as metformin to the mammal) can be effective to reduce the level of IL-6R polypeptides (e.g., IL-6Rα) on one or more cells (e.g., on the surface of one or more cells) within the mammal. For example, administering one or more biguanides to a mammal can reduce the level of IL-6R polypeptide expression on any appropriate type of cell within the mammal. Examples of cells on which one or more biguanides can reduce the level of IL-6R polypeptide expression include, without limitation, hepatocytes, epithelial cells, B-cells, plasma cells, monocytes, and macrophages. Any appropriate method can be used to determine a level of IL-6R polypeptide expression by cells within a mammal. Examples of methods that can be used to determine a level of IL-6R polypeptide expression include, without limitation, western blotting techniques, ELISA, real-time PCR, flow cytometry, mass spectrometry, and a Luminex assay.

In some cases, treating a mammal having, or at risk of developing CRS, as described herein (e.g., by administering one or more biguanides such as metformin to the mammal) can be effective to reduce the level of CRP polypeptides (e.g., CRP polypeptides produced by one or more cells liver cells) within the mammal. For example, administering one or more biguanides to a mammal can reduce the level of CRP polypeptides within the mammal. Any appropriate method can be used to determine a level of CRP polypeptides within the mammal. Examples of methods that can be used to determine a level of CRP polypeptides include, without limitation, western blotting techniques, ELISA, real-time PCR, flow cytometry, mass spectrometry, and a Luminex assay.

In some cases, one or more biguanides (e.g., metformin) can be formulated into a composition (e.g., a pharmaceutically acceptable composition) for administration to a mammal having CRS or being at risk for developing CRS. For example, one or more biguanides can be formulated together with one or more pharmaceutically acceptable carriers (additives) and/or diluents. Pharmaceutically acceptable carriers, fillers, and vehicles that may be used in a pharmaceutical composition described herein include, without limitation, dimethyl sulfoxide (DMSO), ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, and wool fat.

A composition including one or more biguanides (e.g., metformin) can be designed for oral or parenteral (including subcutaneous, intramuscular, intravenous, and intradermal) administration to a mammal (e.g., a human) having, or at risk of developing, CRS. Compositions suitable for oral administration include, without limitation, liquids, tablets, capsules, pills, powders, gels, and granules. Compositions suitable for parenteral administration include, without limitation, aqueous and non-aqueous sterile injection solutions that can contain anti-oxidants, buffers, bacteriostats, and solutes that render the formulation isotonic with the blood of the intended recipient. In some cases, a composition including one or more biguanides can be formulated for oral administration.

A composition including one or more biguanides (e.g., metformin) can be designed for any type of release (e.g., release of the one or more biguanides from the composition) into the mammal the composition is administered to (e.g., a mammal having, or at risk of developing, CRS). For example, a composition including one or more biguanides can be designed for immediate release, slow release, or extended release.

A composition including one or more biguanides (e.g., metformin) can be administered locally or systemically to a mammal (e.g., a human) having, or at risk of developing, CRS. For example, a composition including one or more biguanides can be administered locally to a mammal (e.g., a human) having, or at risk of developing, CRS by injection into or near a body part (e.g., tissue, cell type, or organ) of the mammal that is affected by, or likely to be affected by, the CRS. For example, a composition including one or more biguanides can be administered systemically by oral administration to a mammal having, or at risk of developing, CRS.

A composition including one or more biguanides (e.g., metformin) can be administered to a mammal (e.g., a human) having, or at risk of developing, CRS in any appropriate dose(s). Effective doses can vary depending on the severity of the CRS, the risk of developing CRS, the route of administration, the age and general health condition of the subject, excipient usage, the possibility of co-usage with other therapeutic treatments such as use of other agents, and the judgment of the treating physician. For example, in cases where a composition includes metformin, the composition can include from about 1 mM to about 80 mM (e.g., from about 5 mM to about 80 mM, from about 10 mM to about 80 mM, from about 15 mM to about 80 mM, from about 20 mM to about 80 mM, from about 30 mM to about 80 mM, from about 40 mM to about 80 mM, from about 50 mM to about 80 mM, from about 60 mM to about 80 mM, about 1 mM to about 70 mM, about 1 mM to about 60 mM, about 1 mM to about 50 mM, about 1 mM to about 40 mM, about 1 mM to about 30 mM, about 1 mM to about 20 mM, about 1 mM to about 10 mM, about 5 mM to about 70 mM, about 20 mM to about 60 mM, about 30 mM to about 50 mM, about 10 mM to about 30 mM, about 20 mM to about 40 mM, about 40 mM to about 60 mM, about 50 mM to about 70 mM, about 1 mM to about 80 mM, about 1 mM, about 5 mM, about 10 mM, about 20 mM, about 40 mM, or about 80 mM) metformin. In some cases, a composition including metformin can include about 10 mM metformin. For example, in cases where a composition includes metformin, the composition can include from about 500 mg to about 2500 mg (e.g., from about 750 mg to about 2500 mg, from about 850 mg to about 2500 mg, from about 1000 mg to about 2500 mg, from about 1200 mg to about 2500 mg, from about 1500 mg to about 2500 mg, from about 2000 mg to about 2500 mg, from about 500 mg to about 2000 mg, from about 500 mg to about 1800 mg, from about 500 mg to about 1500 mg, from about 500 mg to about 1200 mg, from about 500 mg to about 1000 mg, from about 500 mg to about 850 mg, from about 500 mg to about 750 mg, from about 600 mg to about 2000 mg, from about 750 mg to about 1800 mg, from about 850 mg to about 1500 mg, from about 1000 mg to about 1200 mg, about 500 mg, about 750 mg, about 850 mg, or about 1000 mg) metformin. In some cases, a composition including metformin can be a liquid including about 100 mg metformin per mL liquid (e.g., about 500 mg metformin per 5 mL liquid). In some cases, a composition including metformin can be a tablet including about 500 mg metformin, 850 mg metformin, or 1000 mg metformin. In some cases, a composition including metformin can be a pill including about 500 mg metformin, about 750 mg metformin, or about 1000 mg metformin. An effective dose of metformin can be a daily effective dose. In some cases, a composition including metformin can be administered as single dose or a divided dose. An effective amount of a composition including one or more biguanides can be any amount that reduces the severity and/or one or more symptom of a condition being treated (e.g., CRS) without producing significant toxicity to the mammal. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, severity of the CRS, and risk of developing CRS may require an increase or decrease in the actual effective amount administered.

A composition including one or more biguanides (e.g., metformin) can be administered to a mammal (e.g., a human) having, or at risk of developing, CRS in any appropriate frequency. The frequency of administration can be any frequency that reduces the severity of the CRS and/or one or more symptoms of the CRS without producing significant toxicity to the mammal. For example, the frequency of administration can be from about once a day to about ten times a day, from about three times a day to about eight times a day, or from about four times a day to about six times a day. The frequency of administration can remain constant or can be variable during the duration of treatment. As with the effective amount, various factors can influence the actual frequency of administration used for a particular application. For example, the effective amount, duration of treatment, use of multiple treatment agents, route of administration, severity of the CRS, and risk of developing CRS may require an increase or decrease in administration frequency.

A composition including one or more biguanides (e.g., metformin) can be administered to a mammal (e.g., a human) having, or at risk of developing, CRS for any appropriate duration. An effective duration for administering a composition including one or more biguanides can be any duration that reduces the severity of the CRS and/or one or more symptoms of the CRS without producing significant toxicity to the mammal. For example, the effective duration can vary from several days to several months or years to a lifetime. In some cases, the effective duration for the treatment of a CRS can range in duration from about 2 days to about a week, from about 2 days to about a month, or from about a week to about a month. Multiple factors can influence the actual effective duration used for a particular treatment. For example, an effective duration can vary with the frequency of administration, effective amount, use of multiple treatment agents, route of administration, severity of the CRS, and risk of developing CRS.

In some cases, one or more biguanides (e.g., metformin) can be administered to a mammal having, or at risk for developing, CRS as the sole active ingredient. For example, one or more biguanides can be administered to a mammal having, or at risk for developing, CRS as the sole active ingredient used to treat CRS. For example, one or more biguanides can be administered as the sole active ingredient to a mammal in need thereof. For example, when one or more biguanides (e.g., metformin) are administered to a mammal having, or at risk for developing, CRS associated with a cancer immunotherapy, the one or more biguanides can be the sole active ingredient used to treat cancer. For example, one or more biguanides (e.g., metformin) can be administered to a mammal having, or at risk for developing, CRS as the sole active ingredient used to reduce levels of IL-6R polypeptides (e.g., IL-6Rα polypeptides).

In some cases, one or more biguanides (e.g., metformin) can be administered to a mammal having, or at risk for developing, CRS with one or more additional agents/therapies. For example, one or more biguanides can be administered with one or more additional agents/therapies to a mammal in need thereof. For example, one or more biguanides (e.g., metformin) can be administered to a mammal having, or at risk for developing, CRS with one or more agents that activate AMPK (e.g., 5-Aminoimidazole-4-carboxamide ribonucleotide (AICAR)). For example, one or more biguanides (e.g., metformin) can be administered to a mammal having, or at risk for developing, CRS with one or more agents that inhibit mammalian target of rapamycin (mTOR; e.g., rapamycin). For example, one or more biguanides (e.g., metformin) can be administered to a mammal having, or at risk for developing, CRS with one or more additional agents/therapies used to treat CRS. Examples of additional agents/therapies used to treat CRS include, without limitation, antibiotics (e.g., metronidazole, beta lactams such as penicillin, cephalosporins, carbapenems, fluoroquinolones, and macrolides), anti-histamines (e.g., chlorphenamine), corticosteroids (e.g., hydrocortisone, prednisone, and dexamethasone), fever reducers (e.g., acetaminophen), inotropic agents, hydration (e.g., intravenous fluid replacement), and/or correcting overhydration (e.g., by dialysis or with furosemide (e.g., intravenous furosemide)). For example, when one or more biguanides (e.g., metformin) are administered to a mammal having, or at risk for developing, CRS associated with a cancer immunotherapy, the one or more biguanides can be administered with one or more additional agents/therapies used to treat cancer. Examples of additional agents/therapies used to treat cancer include, without limitation, surgery, radiation therapies, chemotherapies, targeted therapies, hormonal therapies, angiogenesis inhibitors, immunosuppressants, immune checkpoint inhibitors, immunomodulatory agents, and/or proteasome inhibitors. For example, one or more biguanides (e.g., metformin) can be administered to a mammal having, or at risk for developing, CRS with one or more additional agents/therapies used to reduce levels of IL-6R polypeptides (e.g., IL-6Rα polypeptides). Examples of additional agents/therapies used to reduce levels of IL-6R polypeptides include, without limitation, anti-IL-6 receptor antibodies (e.g., tocilizumab and siltuximab). In cases where one or more biguanides (e.g., metformin) are used in combination with one or more additional agents/therapies, the one or more additional agents/therapies can be administered at the same time or independently. For example, a composition including metformin can be administered first, and the one or more additional agents/therapies can be administered second, or vice versa.

In certain instances, a course of treatment and the severity of one or more symptoms related to the condition being treated (e.g., CRS) can be monitored. Any appropriate method can be used to determine whether or not the severity of a symptom is reduced. For example, the severity of CRS can be assessed using any appropriate methods and/or techniques, and can be assessed at different time points. For example, levels of CRP in the blood (e.g., serum) of a mammal having, or at risk of developing, CRS can be assessed to determine the severity of the CRS.

In some cases, the methods and materials described herein can be used to treat a mammal having a disease or disorder associated with high levels of IL-6 polypeptides. Examples of diseases and disorders associated with high levels of IL-6 polypeptides include, without limitation, Castleman's disease, neuromyelitis optica spectrum disorders (NMOSDs), refractory Behcet's uveitis, refractory major depressive disorder, schizophrenia, Erdheim-Chester disease, and monoclonal gammopathy of undetermined significance (MGUS).

The invention will be further described in the following examples, which do not limit the scope of the invention described in the claims.

EXAMPLES

Example 1: IL-6Rα (CD126) Expression and Metformin Response

Multiple myeloma is a heterogeneous disease with a complex molecular etiology with several groups characterized by recurrent chromosomal translocation. Consistent with preclinical and clinical studies in other tumor types, all myeloma cells do not have same sensitivity for metformin treatment. Most FDA approved drugs are not equally effective in all patients; hence it is highly desirable to identify a marker that can predict metformin responders and achieve maximum benefits. This example demonstrates that metformin is effective in inhibiting cell proliferation and increasing apoptosis in multiple myeloma. The sensitivity of myeloma cells to metformin can be predicted by cell surface expression of IL-6Rα that can serve as a biomarker for the efficacy of this drug.

Materials and Methods
MTT Assay (3-(4,5-Dimethylthiazol-2-5-Diphenyltetrazolium Bromide (MTT) (Thermo Fisher Scientific, MA, USA) was dissolved in PBS to make 12 mM stock solution. Cells were seeded at 10,000 cells in 50 µl complete medium. Drugs, cytokines and antibodies were added at indicated doses in 50 µl complete medium. Cells were incubated for 72 hours for HMCLs and 48 hours for primary myeloma cells in presence of vehicle control, or metformin (1 mM, 5 mM, 10 mM, 20 mM, 40 mM, and 80 mM). MTT (10 µl) was added to each well and incubated for an additional 2 hours. Lysis buffer (100 µl) was added to each well and absorbance was read at 570 nm.

Flow Cytometry

Cell surface expression of IL-6Rα, IL-6ST, and CD44 was quantified using the fluorescently labeled antibodies anti-IL6R-PE (UV4, Biolegend), anti-IL6ST-APC (2E1B02, Biolegend) and anti-CD44-BV711 (IM7, Biolegend), and compared with isotype control. BrdU labeling assay (Phase-Flow™, Biolegend) was performed according to the manufacturer's protocol to quantify cell cycle. After drug treatment, cells were labeled with BrdU for 2 hours. For apoptosis assay, the cells were treated with metformin for 72 hours and quantified with Annexin V (Biolegend). All flow cytometry experiments were on an LSR Fortessa (Becton Dickinson). The data were analyzed using flowJo vs10.4.2 (Flowjo LLC, USA).

Results

IL-6Rα, also known as CD126, is expressed primarily on hepatocytes, epithelial cells, plasma cells, and B-cells.

Figure 1:
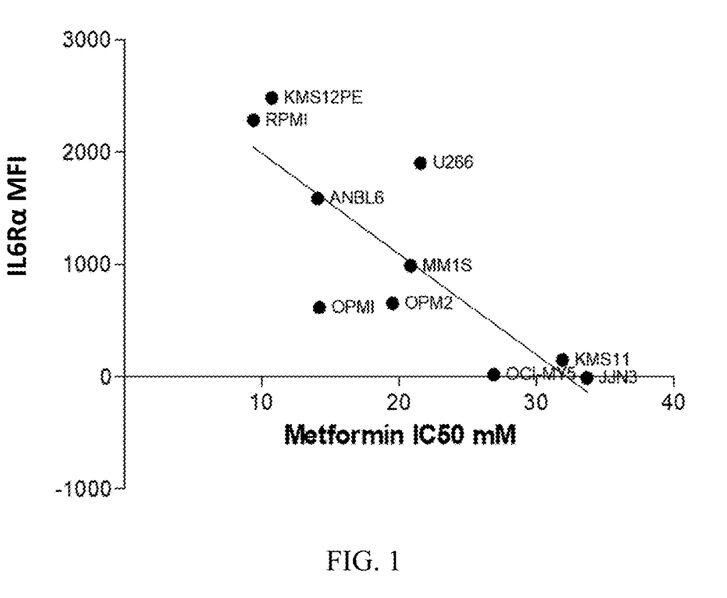
FIG. 1 contains a graph showing a negative correlation between metformin $IC_{50}$ (as determined by MTT assay) and IL-6Rα (CD126) surface expression (as determined by flow cytometer). High cell surface expression of IL-6Rα predicts for better sensitivity of the cell to metformin therapy (and at a lower dose).
Figure 4:
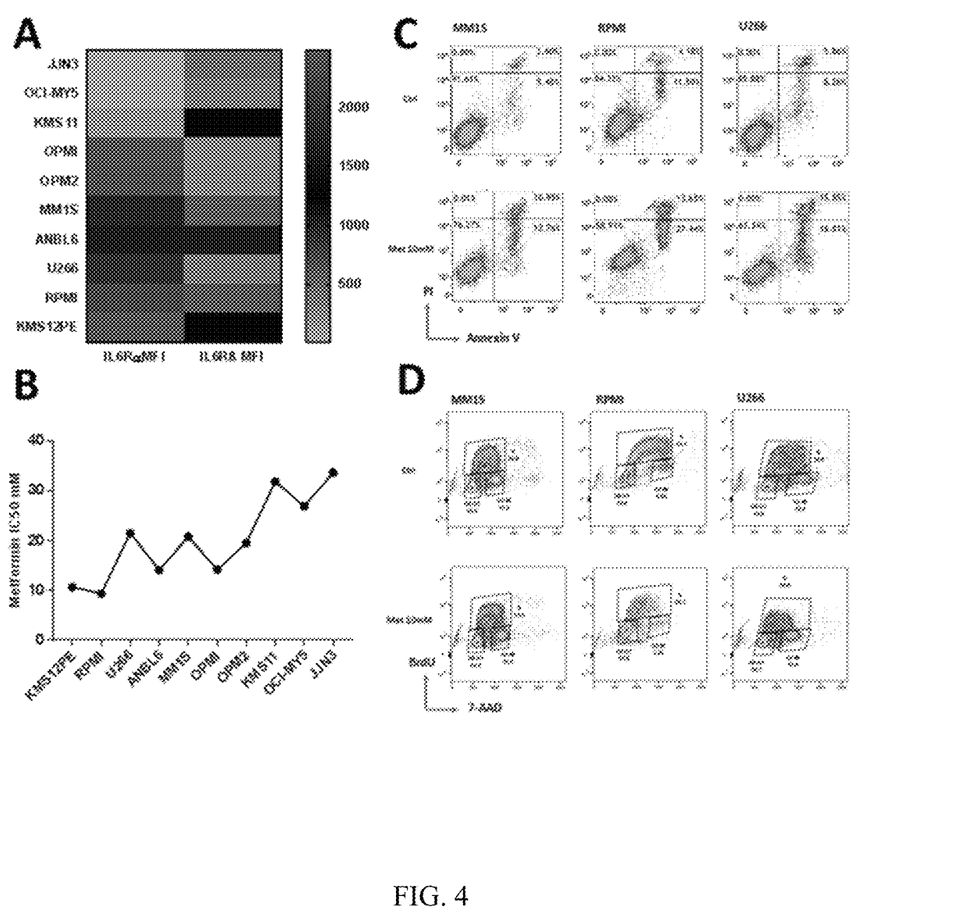

Cell surface expression for IL-6Rα was measured for 10 different human myeloma cell lines (HMCLs) by flow cytometer. IL-6Rα expression varied across HMCLs (FIG. 4A). HMCLs were treated with different doses of metformin for 72 hours and MTT assay was conducted. $IC_{50}$ was calculated using Compusyn software. Metformin $IC_{50}$ showed strong negative correlation to IL-6Rα expression (FIG. 1). RPMI and KMS12PE with highest IL-6Rα expression required less than 10 mM metformin to achieve 50% cell death/growth inhibition. JJN3 with no significant IL-6Rα expression required more than 30 mM metformin for 50% cell death/growth inhibition.

Figure 2:
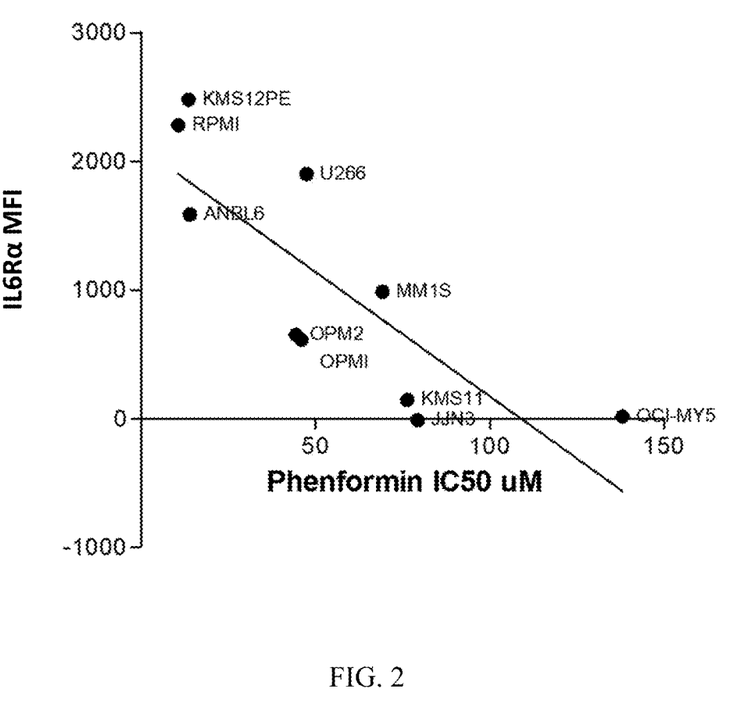
FIG. 2 contains a graph showing a negative correlation between phenformin $IC_{50}$ (as determined by MTT assay) and IL-6Rα (CD126) surface expression (as determined by flow cytometer).

Phenformin, a biguanide having similar mechanism to metformin but having more potency, was also examined. Phenformin $IC_{50}$ also strongly negatively correlated with IL-6Rα expression (FIG. 2). IL-6Rα high expressers were also better phenformin responders.

Figure 3:
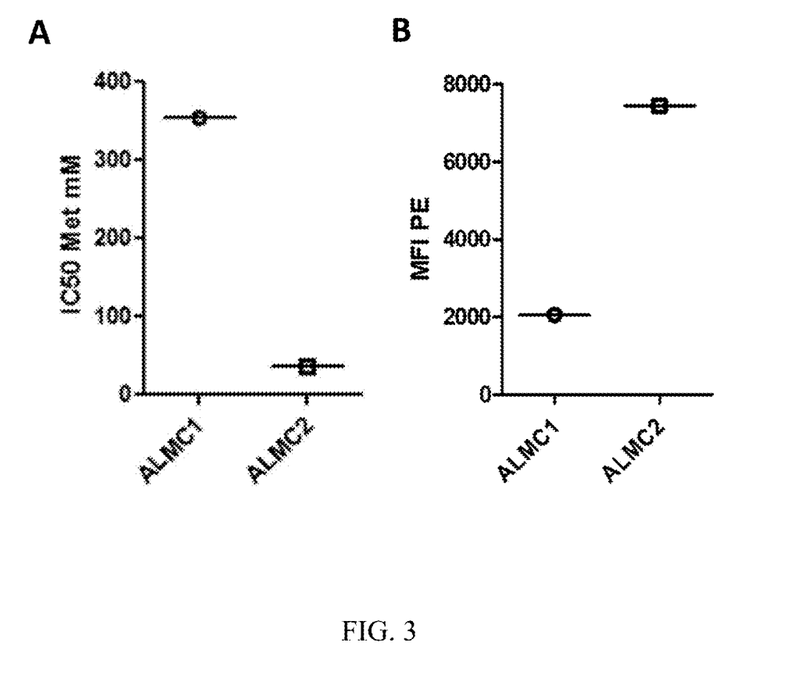
FIGS. 3A-3B contain graphs comparing metformin efficacy in two primary amyloidosis (AL) cell lines, ALMC1 and ALMC2, having different levels of IL-6Rα (CD126). (A) Metformin $IC_{50}$ is lower for ALMC2 compared to ALMC1 (as determined by MTT assay). (B) IL-6Rα expression is higher for ALMC2 compared to ALMC1 (as determined by flow cytometer).

Primary amyloidosis (AL) is plasma cell disorder. Two AL cell lines, ALMC1 and ALMC2, from a patient were characterized. ALMC1 and ALMC2 expressed significantly different level of IL-6Rα (FIG. 3B). ALMC2, a high IL-6Rα expresser, responded better to metformin than low IL-6Rα expresser ALMC1 (FIG. 3A).

These results demonstrate that IL-6Rα cell surface expression level can predict metformin response in multiple myeloma and primary amyloidosis. Further, metformin was effective in inhibiting cell proliferation and increasing apoptosis in multiple myeloma.

Example 2: Diagnostic and Therapeutic Implications of Targeting IL-6 with Metformin Materials and Methods
Cell Culture Human myeloma cells lines (HMCLs) RPMI-8266, U266-B1 and MM1S were purchased from American Type Culture Collection (ATCC, Manassas, Va., USA). OPMI, OPM2, ANBL6, OCI-MYS, JJN3 and KMS12PE were obtained from different laboratories at Mayo Clinic. HMCLs were maintained in RPMI-1640 (Thermo Scientific, Grand Island, N.Y., USA) medium supplemented with 10% heat-inactivated fetal bovine serum (FBS) (Thermo Scientific), 100 U/mL penicillin, and 100 µg/ml streptomycin (Thermo Scientific) in a humidified incubator and 5% $CO_2$ at 37° C. ANBL6 cells were also supplemented with 1 ng/ml recombinant human IL-6 (Biolegend, San Diego, Calif., USA).

Human hepatocellular carcinoma cell line Hep3B was purchased from ATCC. Cells were maintained in DMEM supplemented with 10% FBS and 100 U/mL penicillin and 100 µg/mL streptomycin.

Primary Multiple Myeloma Cells

Approval was obtained from Institution Review Board and all patients provided informed consent. CD138⁺ cells from bone marrow aspirates were enriched using magnetic associated cell sorting at the Hematology Research Core (Mayo Clinic Rochester, USA). Primary myeloma cells were maintained in RPMI supplemented with 10% FBS, antibiotics and 1 ng/mL IL-6.

Inhibitors and Drugs

Metformin (Millipore, Darmstadt, Germany) was dissolved in DMSO. Actemra (tocilizumab) was obtained from the Mayo Clinic Pharmacy.

MTT Assay (3-(4,5-Dimethylthiazol-2-5-Diphenyltetrazolium Bromide (MTT) (ThermoFisher Scientific, MA, USA) was dissolved in PBS to make 12 mM stock solution. Cells were seeded at 10,000 cells in 50 µL complete medium. Drugs, cytokines and antibodies were added at indicated doses in 50 µL complete medium. HMCLs were incubated for 72 hours while primary myeloma cells were incubated for 48 hours in presence of vehicle control, metformin (1 mM, 5 mM, 10 mM, 20 mM, 40 mM and 80 mM). MTT (10 µL) was added to each well and incubated for an additional 2 hours. Lysis buffer (100 µL) was added to each well and absorbance was read at 570 nm. Absorbance under treatment was normalized with average of vehicle control and presented as relative proliferation with respect to control. $IC_{50}$ was calculated using Compusyn software.

Flow Cytometry

Surface expression of IL-6Rα, IL-6ST and CD44 was quantified using IL-6Rα-PE (clone UV4, Biolegend), IL-6ST-APC (2E1B02, Biolegend) and CD44-BV711 (IM7, Biolegend), and compared to isotype or unstained control. BrdU labelling assay (Phase-Flow™, Biolegend) was performed according to the manufacturer's protocol to quantify cell cycle fractions. After treatment cells were labelled with BrdU for 2 hours. For apoptosis assay, cells were treated with metformin for 72 hours and quantified with Annexin V (Biolegend). All assays were quantified on LSR Fortessa. Data were analyzed using flowJo vs10.4.2 (Flowjo LLC, USA).

Enzyme-Linked Immunosorbent Assay

A human soluble IL-6Rα ELISA kit was purchased from ThermoFisher Scientific. Cells were cultured with or without treatment in 12-well plates for 48 hours. Cell conditioned media were collected and protein lysates was prepared from cell pellets. Standard and reagents were prepared as per manufacturer's instructions. Undiluted 100 sample or standard was added per well in duplicates and 40 µL of HRP conjugate to each well. The plate was incubated for 2 hours on a mechanical shaker. After multiple washing, 100 µL TMB substrate solution was added to each well and incubated for 10 minutes in the dark. 100 µL of stop solution was added to each well and absorbance was read at 450 nm. Absolute concentrations of sIL-6R were interpolated from the standard curve.

A CRP ELISA kit was purchased from ThermoFisher Scientific. Hepatocellular cells (Hep3B) were treated either with metformin 10 mM or vehicle control for 72 hours. After pre-treatment, cells were counted and seeded in 24-well plates at density of 30,000 cells in 1 mL culture medium. Metformin pre-treated cells were used for metformin (10 mM), IL-6 (50 ng/ml)+Metformin (10 mM) and IL-6 (50 ng/ml)+Metformin (10 mM)+Tocilizumab (10 µg/ml) group. Vehicle pre-treated cells were used for control, IL-6 (50 ng/ml), IL-6 (50 ng/ml)+Tocilizumab (10 µg/ml) group. After 48 hours of culture, medium was harvested from each group and CRP level was quantified using ELISA kit as per manufacturer's instruction.

Gene Expression

TaqMan assay and relative method (ddCT) were used to quantify gene expression. Total RNA was extracted using RNeasy (Qiagen) kit and quantified for amount and purity with Nanodrop. 2 µg of RNA was converted to cDNA using first strand High-Capacity cDNA reverse transcription kit (ThermoFisher). 10 ng/well in 10 µL reaction per well in duplicate for each samples were used to quantify mRNA. TaqMan Fast Advanced Mastermix (Applied Biosystems) was used and plates were run on ViiA 7 Real-Time PCR system (ThermoFisher Scientific). Data was normalized with two independent house-keeping genes (HPRT1 and ACTB).

IL-6Rα Knock-Down (KD)

pGFP-C-shLenti vectors (4 shRNA targeting IL-6Rα and 1 scramble control) were purchased from Origene. Lentiviral particles were generated in HEK293T cells using pMD2.G (Addgene) and psPAX2 (Addgene). HMCLs were transduced with lentiviral vector particles in the presence of Polybrene (Millipore). Stable cell lines were generated after selecting for GFP positive cells with flow sorting and treatment with puromycin. Decreased expression of IL-6Rα compared to scrambled control was confirmed with qPCR and flow cytometer.

IL-6Rα Over-Expression pCMV3-IL-6R-OFPSpark was purchased from Sinobiological (Wayne, Pa., USA). JJN3 cells were transfected with pCMV-IL-6R plasmid using HD fugene. After geneticin selection, cells were sorted for RFP positive population. IL-6Rα over-expression was confirmed with flow cytometry.

Data Analysis

All experiments were replicated multiple times. GraphPad Prism (v-7.03) was used to generate graph. Data is presented as mean±SEM (standard error of the mean). Student "t" test was used to calculate statistical significance between two groups and ANOVA to compare more than two groups. *$P<0.001$, $P<0.01$ and *$P<0.05$.

Results

Metformin Induced Apoptosis and Inhibited Cell Cycle Progression in Myeloma Cells Independent of their Underlying Genetic Abnormalities.

Toxicity associated with metformin was evaluated in hematologic malignancies, specifically multiple myeloma as well as other plasma cell disorders and cell based therapy for cancer such as chimeric antigen receptor T cells (CAR-T). The in vitro activity of metformin was studied against 10 different human multiple myeloma cell lines (HMCLs) that represent the full spectrum of cytogenetic and FISH abnormalities that occur in multiple myeloma: from hyperdiploidy to translocations such as t(11;14); t(4;14); t(14;16) and deletion of the short arm of chromosome 17 (17p) that is the locus of TP53, perhaps the most important tumor suppressor gene known to humans (Table 1).

TABLE 1

Characterization of HMCLs used in these studies. Chromosomal abnormality (CA), targeted genes, RAS and p53 mutations status (wild type (WT) and mutated (Mut)). All three groups of HMCLs based on IL-6 signaling (independent, autocrine and dependent) were included.

| HMCLs | CA | Target genes | RAS | TP53 | IL6 group |
|---|---|---|---|---|---|
| KMS12PE | t(11;14) | CCND1 | WT | Mut | Independent |
| RPMI | t(14;16) | c-Maf | Mut | Mut | Independent |
| U266 | t(11;14) | CCND2 | WT | Mut | Autocrine |
| ANBL6 | t(14;16) | c-Maf | WT | Mut | Dependent |
| MM1S | t(14;16) | c-Maf | Mut | WT | Independent |
| OPM1 | t(4;14) | MMSET/FGFR3 | WT | Mut | Independent |
| OPM2 | t(4;14) | MMSET/FGFR3 | WT | Mut | Independent |
| KMS11 | t(4;14) | MMSET/FGFR3 | WT | Mut | Independent |
| OCI-MYS | t(14;16) | c-Maf | WT | Mut | Independent |
| JJN3 | t(14;16) | c-Maf | Mut | Mut | Independent |
| KP6 | Hyperdiploid | | | | |

In vitro studies showed that metformin inhibited survival/growth of multiple myeloma cells with variable levels of efficacy (FIG. 4B). The effect of metformin on two hallmarks of cancer cells, cell proliferation and apoptosis, was also analyzed. In MM1S, RPMI and U266 cells, metformin increased apoptosis (FIG. 4C). The percentage of live cells after metformin treatment decreased to 59% in RPMI while in U266 and MM1S decreased to 67% and 76% respectively. Next the effect of metformin on cell cycle progression was examined using the BrdU assay. BrdU assay is also used clinically in myeloma at diagnosis and at relapse to determine the 'S phase' fraction. Similar to what was observed in the apoptosis assay, a reduction in the S phase fraction was found in response to metformin from 53% to 29% in RPMI, 35% to 20% in U266 and 34% to 23% in MM1S after metformin treatment (FIG. 4D) (all changes are highly statistically significant).

IL-6Rα Expression on the Myeloma Cell Surface Predicted for Response to Metformin Therapy and can Serve as a Biomarker for Therapeutic Response.

Figure 5:
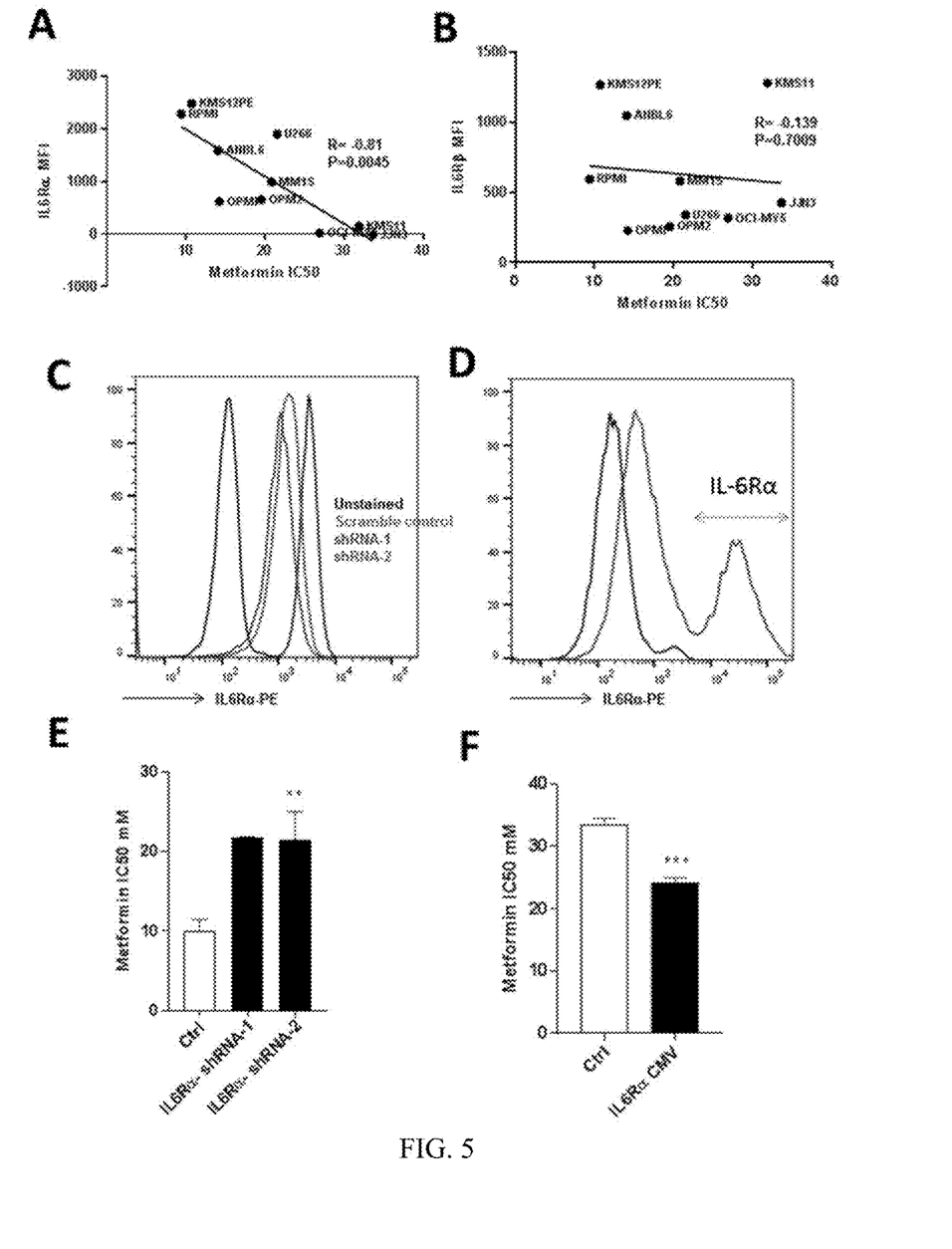

HMCLs were evaluated for basal expression of several components of IL-6 signaling (IL-6, IL-6Rα, and IL-6ST) (FIG. 4A) and CD44. HMCLs that represent the full spectrum of multiple myeloma subtypes and have frequent genetic abnormalities including mutations in TP53 and KRAS were included (Table 1). Irrespective of the underlying chromosomal abnormalities and driver mutations, surface expression of IL-6Rα predicted the response to metformin therapy (p=−0.81, p=0.0045) (FIG. 5A). There was no significant correlation between response to metformin and cell surface expression of IL-6ST (p=−0.14, p=0.7009) (FIG. 5B). Note that IL-6ST is also known as IL-6Rβ. To further confirm this, IL-6Rα was silenced in RPMI cells (FIG. 5C) and the sensitivity of the cells to metformin ($IC_{50}$) was quantitated. Consistent with the correlation data from FIG. 5A, the $IC_{50}$ for metformin significantly increased in RPMI IL-6Rα knock-downs compared to the scramble control (FIG. 5E). To further confirm this, IL-6Rα was transiently over-expressed in JJN3 (FIG. 5D), that naturally expresses very low levels of IL-6-Rα (FIG. 4A). Compared to wild type JJN3, the $IC_{50}$ for metformin significantly decreased in JJN3 engineered to over-express IL-6Rα (FIG. 5F).

Metformin Killed Myeloma Cells by Down-Regulating IL-6Rα Expression and Negating the Growth and Survival Signal of IL-6 on Myeloma Cells.

Figure 6:
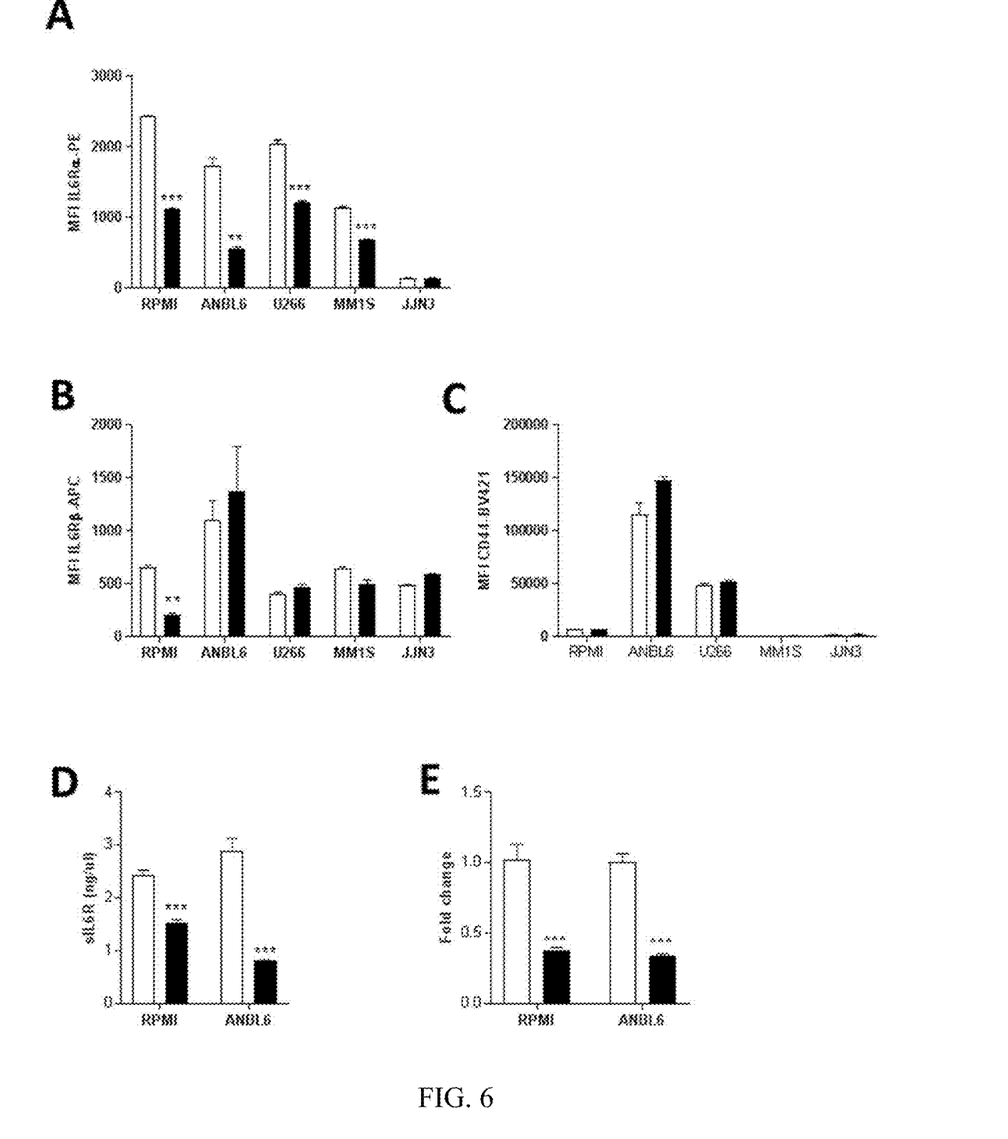
FIGS. 6A-6E show that metformin killed myeloma cells by down-regulating IL-6Rα expression and negating the growth and survival signal of IL-6 on myeloma cells. RPMI, ANBL6, U266, MM1S, and JJN3 were treated with metformin 10 mM for 72 hours and median fluorescence intensity for cell surface expression of (A) IL-6Rα, (B) IL-6-Rβ and (C) CD44 was quantified using flow cytometry. Vehicle (open bar) and metformin 10 mM (shaded bar), n=3. (D) RPMI and ANBL6 cells were cultured either in the presence of vehicle control or metformin 10 mM for 72 hours. Soluble IL-6Rα was quantified in media supernatant using ELISA kit. Vehicle (open bar) and metformin 10 mM (shaded bar), n=6. Metformin decreased the concentration of soluble IL-6Rα in the media. (E) RPMI and ANBL6 cells were cultured either in presence of vehicle control or metformin 10 mM for 72 hours. mRNA expression of IL-6Rα was quantified using qPCR TaqMan assay. Vehicle (open bar) and metformin 10 mM (shaded bar), n=6. Metformin decreased the expression of IL-6Rα at the level of transcription.

To evaluate whether metformin directly modulates IL-6 signaling by altering the expression of components of the IL-6 signaling cascade, HMCLs were cultured in the presence or absence of metformin and IL-6 (ELISA, data not presented), IL-6Rα and IL-6Rβ expression was measured by flow cytometry. Indeed, metformin significantly and consistently reduced cell surface expression of IL-6Rα (FIG. 6A) but not IL-6Rβ (FIG. 6B). Concomitantly, no significant change in CD44 expression across the same HMCLs was found (FIG. 6C). This ruled out global decrease in protein expression and suggested a direct and specific inhibition of IL-6Rα expression by metformin. Furthermore, it was investigated whether metformin induced a decreased in cell surface IL-Rα by inducing shedding of IL-6Rα as this might decrease classical IL-6 signaling but promote trans-IL-6 signaling. A decrease in soluble IL-6Rα was observed (FIG. 6D) suggesting that the decrease in IL-6Rα expression is at the level of gene transcription and not due to shedding of IL-6Rα from the cell surface. To further validate this, IL-6Rα expression was examined at the mRNA level after metformin treatment. Metformin decreased the level of IL-6Rα transcription (FIG. 6E) and therefore, effectively it inhibits both classical and trans IL-6 signaling. Additional studies showed that inhibition of IL-6Rα mRNA levels is due to mIR-34a that is stimulated via the down-regulation of the mTOR pathway.

Metformin Kills Primary Myeloma Cells by Down-Regulating IL-6Rα Expression.

Figure 7:
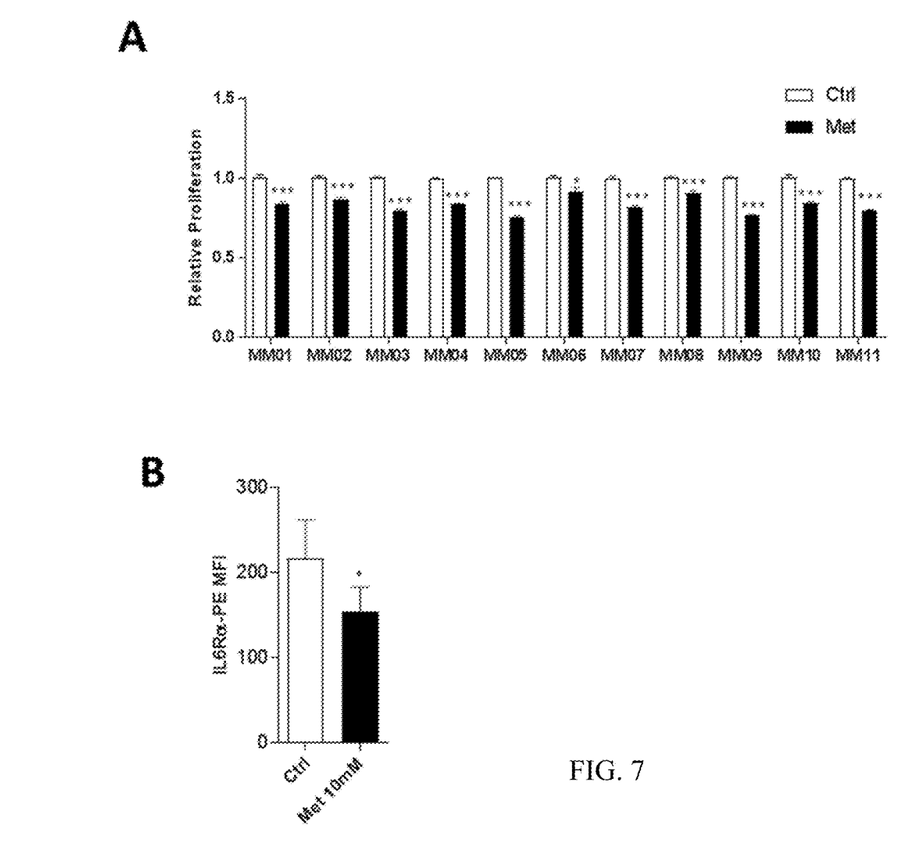
FIGS. 7A-7B show that metformin killed primary myeloma cells by down-regulating IL-6Rα expression. (A) Bone marrow aspirates were enriched for multiple myeloma cells by with magnetic associated cell sorting using CD138+ (a marker for myeloma cells). Cells were treated with metformin 10 mM or vehicle control. After 48 hours of culture, the MTT assay was performed to determine the percentage of live cells. Data is presented as relative proliferation compared to vehicle control (n=6 per sample). (B) CD138+ enriched cells were cultured for 48 hours either with vehicle control or metformin 10 mM. Cells were stained with IL-6Rα-PE antibody. Data is presented as median fluorescence intensity (n=11). Metformin reduced cell surface expression of IL-6Rα on primary multiple myeloma cells.

To validate our observations in HMCLs, in vitro experiments were perform on primary myeloma cells isolated from patients with multiple myeloma. The primary myeloma cells studied also covered the known spectrum of cytogenetic and FISH abnormalities seen with this disease (hyperdiploidy, t(11;14), t(4;14), 17p-, 1q amplification and c-MYC disruption). The same results were observed as in HMCLs, namely that metformin decreased survival/proliferation of primary myeloma cells (FIG. 7A) and decreased cell surface expression of IL-6Rα (FIG. 7B).

Metformin Down-Regulated IL-6Rα Expression on Hepatocytes.

Figure 8:
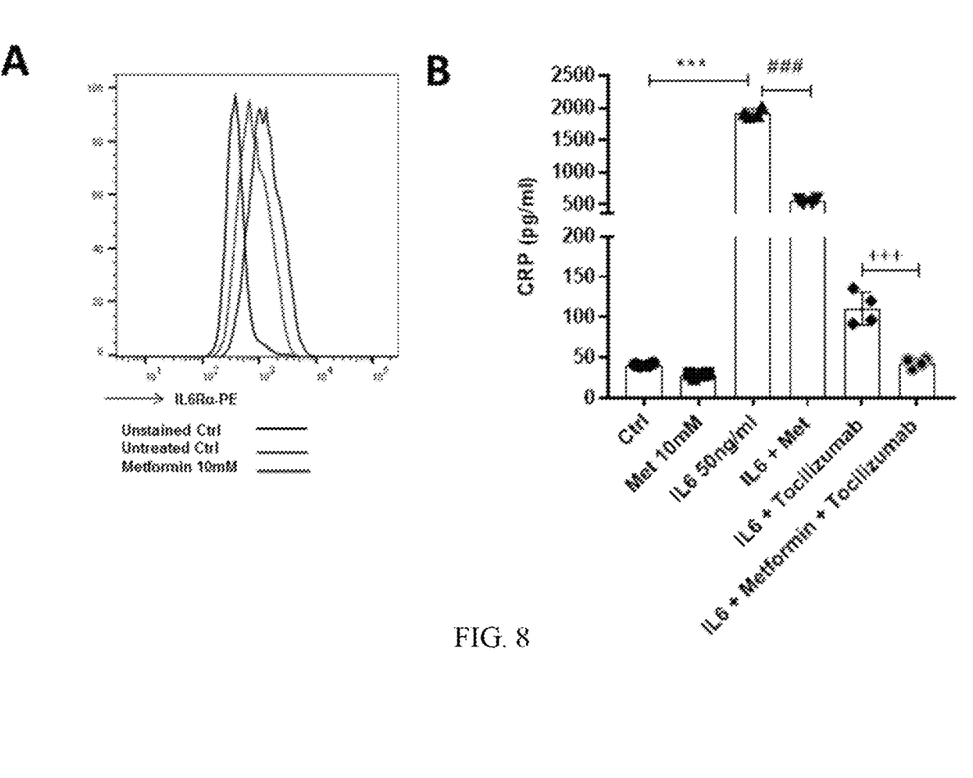
FIGS. 8A-8B show that metformin was effective in preventing C-reactive protein (CRP) release from hepatocytes after IL-6 stimulation. Hepatoma cell line (Hep3b) was pre-treated with metformin (10 mM) or vehicle for 72 hours. (A) Cells were stained with IL-6Rα-PE and data was acquired on BD Fortessa. Data is presented as histogram. Unstained control was used as background control. Metformin decreased expression of IL-6Rα on the surface of hepatocytes. (B) CRP release after stimulation of hepatocytes with IL-6. After treatment equal numbers of cells were seeded in each well (30,000 cells/ml) in 24-well plate. Cells were treated for 48 hours with different combinations (Ctrl: Vehicle control; Met: Metformin 10 mM; IL-6: Interleukin 6 (50 ng/ml); Tocilizumab 10 µg/mL). Media were harvested and CRP was measured with a human CRP ELISA kit (Thermo Scientific) (n=4 per sample). Metformin pretreatment reduced CRP release from hepatocytes in response to IL-6 stimulation. Metformin and tocilizumab reduced CRP production by hepatocytes to normal after stimulation with IL-6. In other words, metformin with tocilizumab neutralized the effect of IL-6 on hepatocyte CRP release.

With the discovery of this novel mechanism of action for metformin (i.e. specific down-regulation of IL-6Rα and efficacy against multiple myeloma), it was determined whether metformin has therapeutic potential in other disease states where IL-6 may play an important or key pathologic role. Physiologically, IL-6Rα is selectively expressed by B-lymphocytes, plasma cells, hepatocytes and some epithelial cells. In the pathogenesis of CRS, IL-6 signaling plays an important role, especially on hepatocytes. The potential of metformin to decrease IL-6Rα expression on hepatocytes was evaluated. Consistent with the observations in HMCLs and primary myeloma samples, hepatocytes expressed IL-6Rα and upon metformin treatment, expression of the receptor decreased (FIG. 8A).

Metformin was Effective in Preventing CRP Release from Hepatocytes after IL-6 Stimulation.

In patients treated with CAR-T cell therapy or BiTE, CRP levels are routinely measured in the blood to monitor for CRS. Increased levels of IL-6 activate IL-6 signaling via IL-6Rα on hepatocytes and in response, CRP is produced by hepatocytes. Since metformin decreased hepatocyte IL-6Rα expression, it was determined whether it could inhibit IL-6 signaling and block CRP production. Indeed metformin significantly inhibited IL-6 induced CRP production from hepatocytes (FIG. 8B).

The Combination of Metformin and Tocilizumab was Superior to Either Alone in Suppressing CRP Release from the Liver and May be Optimal for Prevention and Therapy of CRS.

At present, tocilizumab is prescribed for the treatment of ongoing CRS. It was examined if metformin will have an additive effect in inhibiting CRP production from hepatocytes in response to IL-6 stimulation. The combination of metformin and tocilizumab at the given concentration were able to reduce CRP levels to baseline suggesting that the combination can control CRS significantly better than tocilizumab alone (FIG. 8B). Moreover, pretreatment with metformin may prevent CRS from developing in the first place.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having cytokine release syndrome (CRS), wherein said method comprises:
   (a) identifying said mammal as having said CRS, and
   (b) administering to said mammal a composition comprising a biguanide, wherein the severity of said CRS is reduced within said mammal.

2. The method of claim 1, wherein said mammal is a human.

3. The method of claim 1, wherein said biguanide is metformin.

4. The method of claim 1, wherein said CRS is associated with an immunotherapy.

5. The method of claim 4, wherein said immunotherapy comprises chimeric antigen receptor T (CAR-T) cell therapy.

6. A method for treating a mammal at risk of developing CRS, wherein said mammal is scheduled to undergo CAR-T cell therapy, wherein said method comprises:
   (a) identifying said mammal as being at risk of developing CRS, and
   (b) administering to said mammal a composition comprising a biguanide to reduce the risk of said CRS within said mammal following said CAR-T cell therapy.

7. The method of claim 6, wherein said mammal is a human.

8. The method of claim 6, wherein said biguanide is metformin.

9. The method of claim 6, wherein said composition comprising said biguanide is administered to said mammal prior to said CAR-T cell therapy.

10. The method of claim 6, wherein said composition comprising said biguanide is administered to said mammal concurrent with said CAR-T cell therapy.

11. The method of claim 6, wherein said mammal does not develop said CRS following said administering step.

* * * * *